(12) United States Patent
Noda et al.

(10) Patent No.: US 12,099,297 B2
(45) Date of Patent: Sep. 24, 2024

(54) ENERGY-SENSITIVE COMPOSITION, CURED PRODUCT, AND FORMING METHOD OF PATTERNED CURED PRODUCT

(71) Applicants: TOKYO OHKA KOGYO CO., LTD., Kawasaki (JP); Tokyo University of Science Foundation, Tokyo (JP)

(72) Inventors: Kunihiro Noda, Kawasaki (JP); Dai Shiota, Kawasaki (JP); Koji Arimitsu, Tokyo (JP)

(73) Assignees: TOKYO OHKA KOGYO CO., LTD., Kawasaki (JP); Tokyo University of Science Foundation, Tokyo (JP)

( * ) Notice: Subject to any disclaimer, the term of this patent is extended or adjusted under 35 U.S.C. 154(b) by 423 days.

(21) Appl. No.: 17/452,343

(22) Filed: Oct. 26, 2021

(65) Prior Publication Data

US 2022/0146929 A1 May 12, 2022

(30) Foreign Application Priority Data

Nov. 6, 2020 (JP) ................. 2020-185802

(51) Int. Cl.
| | |
|---|---|
| G03F 7/004 | (2006.01) |
| C07D 233/60 | (2006.01) |
| C07D 311/86 | (2006.01) |
| C07F 9/06 | (2006.01) |
| G03F 7/075 | (2006.01) |

(52) U.S. Cl.
CPC ......... *G03F 7/0045* (2013.01); *C07D 233/60* (2013.01); *C07D 311/86* (2013.01); *C07F 9/067* (2013.01); *G03F 7/0757* (2013.01)

(58) Field of Classification Search
None
See application file for complete search history.

(56) References Cited

U.S. PATENT DOCUMENTS

| | | |
|---|---|---|
| 6,174,982 B1 | 1/2001 | Nishida et al. |
| 6,251,558 B1 | 6/2001 | Elian et al. |
| 2003/0036015 A1 | 2/2003 | Fedynyshyn |
| 2004/0259029 A1 | 12/2004 | Nagahara et al. |
| 2009/0136869 A1 | 5/2009 | Ogihara et al. |
| 2010/0009289 A1 | 1/2010 | Fedynyshyn |
| 2011/0097669 A1 | 4/2011 | Fukui et al. |
| 2015/0338734 A1* | 11/2015 | Noda ................ C08G 73/1042 430/325 |
| 2016/0009737 A1 | 1/2016 | Ikeda et al. |
| 2016/0122292 A1 | 5/2016 | Sakai et al. |
| 2017/0184964 A1 | 6/2017 | Hatakeyama et al. |
| 2018/0187010 A1 | 7/2018 | Chisaka et al. |
| 2019/0332010 A1* | 10/2019 | Noda ..................... C08G 77/12 |

FOREIGN PATENT DOCUMENTS

| | | |
|---|---|---|
| JP | H08-305028 A | 11/1996 |
| JP | 2009-126940 A | 6/2009 |
| JP | 2011-080032 A | 4/2011 |
| JP | 2019-194692 A | 11/2019 |
| WO | WO 2014/208632 A1 | 12/2014 |
| WO | WO 2017/007010 A1 | 1/2017 |
| WO | WO 2020/170934 A1 | 8/2020 |

* cited by examiner

*Primary Examiner* — Sean M DeGuire
*Assistant Examiner* — Andrew Preston Traywick
(74) *Attorney, Agent, or Firm* — Knobbe, Martens, Olson & Bear, LLP

(57) ABSTRACT

An energy-sensitive composition including a polysilane, a base generator, and a solvent, the base generator including a compound represented by formula (b1) and a photo base generator:

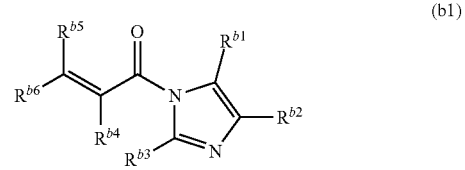

(b1)

in which $R^{b1}$ to $R^{b3}$ each independently represents a hydrogen atom, halogen atom, hydroxyl group, mercapto group, sulfide group, silyl group, silanol group, nitro group, nitroso group, sulfonato group, phosphino group, phosphinyl group, phosphonato group or organic group; $R^{b4}$ and $R^{b5}$ each independently represent a hydrogen atom, halogen atom, hydroxyl group, mercapto group, sulfide group, silyl group, silanol group, nitro group, nitroso group, sulfino group, sulfo group, sulfonato group, phosphino group, phosphinyl group, phosphono group, phosphonato group or aliphatic group; and $R^{b6}$ represents a hydrogen atom, alkyl group or alkoxy group.

8 Claims, No Drawings

ENERGY-SENSITIVE COMPOSITION, CURED PRODUCT, AND FORMING METHOD OF PATTERNED CURED PRODUCT

This application claims priority to Japanese Patent Application No. 2020-185802, filed Nov. 6, 2020, the entire content of which is incorporated herein by reference.

BACKGROUND OF THE INVENTION

Field of the Invention

The present invention relates to an energy-sensitive composition, a cured product, and a forming method of a patterned cured product.

Related Art

Polysilanes having a silicon-silicon bond have been used in applications, for example, ceramic precursors, optoelectronic materials (for example, optoelectronic photographic materials such as photoresists and organic photoreceptors, optical transmission materials such as optical waveguides, optical recording materials such as optical memories, materials for electroluminescence elements), interlayer insulating films and protective films in various elements, sealing materials of light-emitting elements such as LED elements and organic EL elements, coating films for diffusion of impurities to semiconductor substrates, gap filling materials for semiconductor process and the like.

Various compositions containing a polysilane have been developed. For example, an energy-sensitive composition containing a polysilane, and a base generator has been developed (see, Patent Document 1, etc.). In such an energy-sensitive composition, an increase in molecular weight of the polysilane occurs by an action of a base generated from the base generator, to give a cured product. The cured product can be used the materials mentioned above.

Patent Document 1: Japanese Unexamined Patent Application, Publication No. 2019-194692

SUMMARY OF THE INVENTION

When a patterned cured product is formed using such an energy-sensitive composition, a photo base generator is used as the base generator, and regioselective exposure and development is performed on a coating film of the energy-sensitive composition. However, the use of the photo base generator suffers from the disadvantage of lower hardness of the resulting patterned cured product.

In light of the above problems of the prior art, an object of the present invention is to provide an energy-sensitive composition that yields a patterned cured product having higher hardness, a cured product of the energy-sensitive composition, and a forming method of a patterned cured product.

The present inventors have found that an energy-sensitive composition containing a polysilane (A) and a base generator (B), in which the base generator (B) includes a compound represented by the following formula (b1), and a photo base generator, solves the problems, thus completing the present invention. Specifically, the present invention provides the following.

A first aspect of the present invention relates to an energy-sensitive composition containing a polysilane (A), a base generator (B), and a solvent (S), wherein the base generator (B) includes a compound represented by the following formula (b1), and a photo base generator,

[Chem. 1]

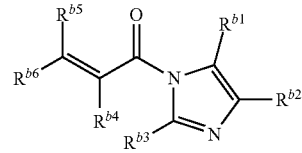

wherein in the formula (b1), $R^{b1}$ to $R^{b3}$ each independently represent a hydrogen atom, a halogen atom, a hydroxyl group, a mercapto group, a sulfide group, a silyl group, a silanol group, a nitro group, a nitroso group, a sulfonato group, a phosphino group, a phosphinyl group, a phosphonato group, or an organic group; $R^{b4}$ and $R^{b5}$ each independently represent a hydrogen atom, a halogen atom, a hydroxyl group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, or an aliphatic group; and $R^{b6}$ represents a hydrogen atom, an alkyl group, or an alkoxy group.

A second aspect of the present invention relates to a cured product of the energy-sensitive composition according to the first aspect.

A third aspect of the present invention relates to a method for forming a patterned cured product, including: applying the energy-sensitive composition according to the first aspect onto a substrate to form a coating film, regioselectively exposing the coating film, developing the exposed coating film, and heating the developed coating film.

According to the present invention, it is possible to provide an energy-sensitive composition which yields a patterned cured product having higher hardness.

DETAILED DESCRIPTION OF THE INVENTION

Embodiments of the present invention will be described in detail below, but the present invention is not limited to the following embodiments and can be implemented by appropriately introducing variations within the object of the present invention. "To" in phrases of the type of "a lower limit to an upper limit" as used herein means a range between the lower limit and the upper limit inclusive, unless otherwise specified.

<<Energy-Sensitive Composition>>

An energy-sensitive composition contains a polysilane (A), and a base generator (B). The base generator (B) includes a compound represented by formula (b1), and a photo base generator. Hereinafter, essential components and optional components contained in the energy-sensitive composition, as well as a production method and applications of the energy-sensitive composition will be described.

<Polysilane (A)>

The structure of the polysilane (A) contained in the energy-sensitive composition is not particularly limited. The polysilane (A) may be linear, branched, network-like, or cyclic, and a linear or branched chain structure is preferable. The polysilane (A) may contain a silanol group or an alkoxy group. A suitable polysilane (A) is exemplified by a polysilane which includes at least one of the units represented by the following formulas (a1) and (a2) as an essential unit, and may contain at least one unit selected from the units represented by the following formulas (a3) to (a5). Such a polysilane may contain a silanol group, or an alkoxy group bonded to a silicon atom.

[Chem. 2]

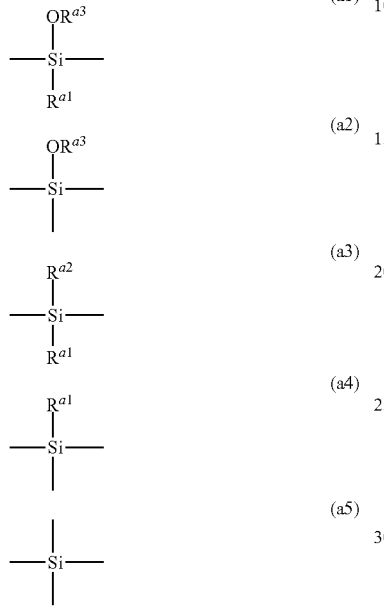

In the formulas (a1) to (a5), $R^{a1}$ and $R^{a2}$ each independently represent a hydrogen atom, an organic group or a silyl group; and $R^{a3}$ represents a hydrogen atom or an alkyl group.

When $R^{a3}$ is an alkyl group, an alkyl group having 1 or more and 4 or less carbon atoms is preferable, and a methyl group and an ethyl group are more preferable.

With regard to $R^{a1}$ and $R^{a2}$, examples of the organic group include a hydrocarbon group such as an alkyl group, an alkenyl group, a cycloalkyl group, a cycloalkenyl group, an aryl group and an aralkyl group, an alkoxy group, an alkenyloxy group, a cycloalkoxy group, a cycloalkenyloxy group, an aryloxy group, an aralkyloxy group, and the like. Among these groups, an alkyl group, an aryl group, and an aralkyl group are preferable. The alkyl group is preferably a linear or branched alkyl group having 1 or more and 20 or less carbon atoms, and more preferably a linear or branched alkyl group having 1 or more and 4 or less carbon atoms. Suitable examples of the aryl group include the following groups.

[Chem. 3]

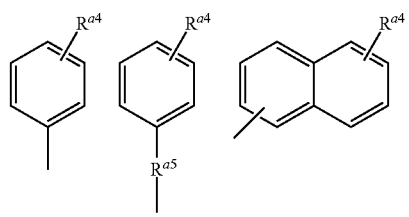

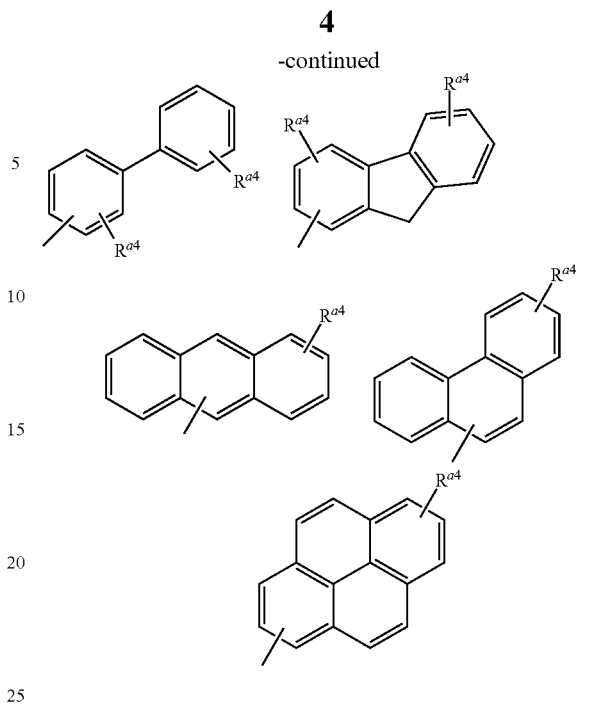

In the above formulas, $R^{a4}$ represents: a hydrogen atom; a hydroxyl group; an alkoxy group such as a methoxy group, an ethoxy group, a butoxy group, and a propoxy group; or a hydrocarbon group such as a methyl group, an ethyl group, a butyl group, and a propyl group. In the above formulas, $R^{a5}$ represents an alkylene group such as a methylene group, an ethylene group, a propylene group, or a butylene group.

Suitable specific examples of the aryl group or aralkyl group include a benzyl group, a phenethyl group, a phenyl group, a naphthyl group, an anthracenyl group, a phenanthryl group, a biphenylyl group, a fluorenyl group, pyrenyl group, and the like.

When $R^{a1}$ and $R^{a2}$ are each a silyl group, examples of the silyl group include $Si_{1-10}$ silanyl groups ($Si_{1-6}$ silanyl groups, etc.) such as a silyl group, a disilanyl group, and a trisilanyl group. The polysilane preferably includes any of the following units (a6) to (a9):

[Chem. 4]

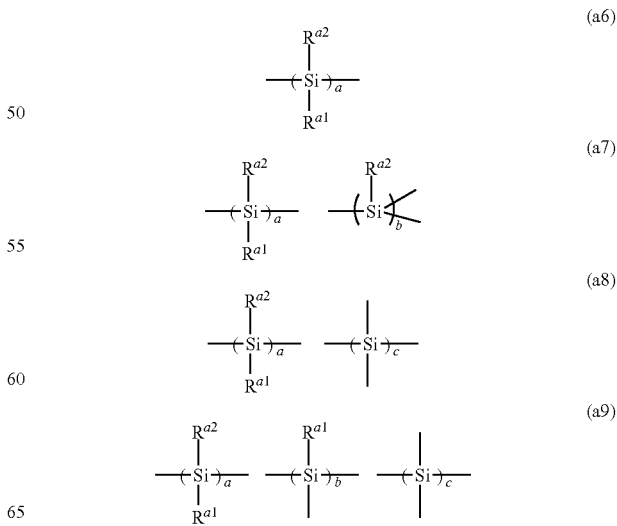

wherein, in the formulas (a6) to (a9), $R^{a1}$ and $R^{a2}$ are the same as $R^{a1}$ and $R^{a2}$ in the formulas (a1), (a3) and (a4); and the symbols a, b, and c are each an integer of 2 or more and 1,000 or less. The symbols a, b, and c are each preferably 3 or more and 500 or less, and more preferably 5 or more and 100 or less. Each constituent unit may be included at random, or in a block-like manner.

Among the polysilanes described hereinabove, a polysilane including an alkyl group in combination with an aryl group or an aralkyl group, wherein the alkyl group, the aryl group and the aralkyl group are each bonded to a silicon atom, or a polysilane having only an alkyl group bonded to a silicon atom is preferable. More particularly, a polysilane including a methyl group in combination with a benzyl group, wherein the methyl group and the benzyl group are each bonded to a silicon atom, a polysilane including a methyl group in combination with a phenyl group, wherein the methyl group and the phenyl group are each bonded to a silicon atom, or a polysilane having only a methyl group bonded to a silicon atom is preferably used.

The mass average molecular weight of the polysilane is preferably 300 or more and 100,000 or less, more preferably 500 or more and 70,000 or less, and still more preferably 800 or more and 30,000 or less, in terms of polystyrene. Two or more types of polysilanes having different mass average molecular weights may be mixed.

The content of the polysilane (A) in the energy-sensitive composition is not particularly limited, and may be adjusted according to a desired film thickness. In view of film-forming properties, the content of the polysilane (A) in the energy-sensitive composition is preferably 1% by mass or more and 50% by mass or less, more preferably 5% by mass or more and 40% by mass or less, and particularly preferably 10% by mass or more and 35% by mass or less.

<Base Generator (B)>

The energy-sensitive composition contains, as the base generator (B), a compound represented by the following formula (b1), and a photo base generator. The compound represented by the following formula (b1) is a compound that generates a base upon heating. In other words, the compound represented by the following formula (b1) is a thermal base generator. On the other hand, the photo base generator is a compound that generates a base with the assistance of light (i.e. the photo base generator is a compound that generates a base upon exposure to light). It should be noted that the photo base generator may be a compound capable of generating a base upon heating, so long as the compound generates the base with the assistance of light. In this specification, a compound that generates a base with the assistance of light and also generates a base upon heating is referred to as a photo base generator. The base generated by the photo base generator with the assistance of light, and the base generated by the compound represented by the following formula (b1) upon heating cause an increase in molecular weight of the polysilane (A) to occur, resulting in the formation of a cured product.

In a method including the steps of: applying a material to form a coating film; regioselectively exposing the coating film; developing the exposed coating film; and heating the developed coating film, the use of such an energy-sensitive composition as the material for coating film formation enables a patterned cured product having higher hardness to be formed, as described later in Examples. The pencil hardness of the patterned cured product is, for example, 3H or higher (harder), and preferably 4H or higher. The use of the photo base generator allows for curing and patterning by the exposure and development, and the use of the compound represented by the formula (b1) allows for further curing upon subsequent heating. It is inferred that the compound represented by the formula (b1) is unlikely to inhibit the curing caused by the photo base generator, probably because of its maximum absorption wavelength ($\lambda_{max}$) of 280 nm or less, and causes further curing to occur upon post-exposure heating, and thus, a patterned cured product having higher hardness can be formed using the energy-sensitive composition described above. On the other hand, when the energy-sensitive composition does not contain the compound represented by the formula (b1), the patterned cured product formed has lower hardness.

[Compound Represented by Formula (b1)]

The energy-sensitive composition contains a compound represented by the following formula (b1). The compound represented by the formula (b1) can decompose by heat, and generate an imidazole compound represented by the following formula (i), which is a base:

[Chem. 5]

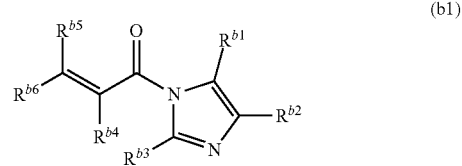

wherein, in the formula (b1), $R^{b1}$ to $R^{b3}$ each independently represent a hydrogen atom, a halogen atom, a hydroxyl group, a mercapto group, a sulfide group, a silyl group, a silanol group, a nitro group, a nitroso group, a sulfonato group, a phosphino group, a phosphinyl group, a phosphonato group, or an organic group; $R^{b4}$ and $R^{b5}$ each independently represent a hydrogen atom, a halogen atom, a hydroxyl group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, or an aliphatic group; and $R^{b6}$ represents a hydrogen atom, an alkyl group, or an alkoxy group, and

[Chem. 6]

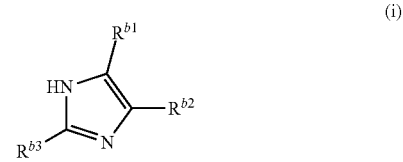

wherein in the formula (i), $R^{b1}$ to $R^{b3}$ are the same as $R^{b1}$ to $R^{b3}$ in the formula (b1).

The organic group in $R^{b1}$ to $R^{b3}$ is exemplified by an alkyl group, an alkenyl group, a cycloalkyl group, a cycloalkenyl group, an aryl group, an aralkyl group, and the like. The organic group may include a bond other than a hydrocarbon group such as a hetero atom, or substituent, therein. In addition, the organic group may be linear, branched or cyclic. The organic group is typically monovalent, and may be a divalent or higher multivalent organic group when the organic group forms a cyclic structure, or the like.

The bond included in the organic group represented by each of $R^{b1}$ to $R^{b3}$ is not particularly limited so long as the effects of the invention are not impaired, and the organic group may include a bond that includes a hetero atom such as an oxygen atom, a nitrogen atom, or a silicon atom. Specific examples of the bond that includes a hetero atom include an ether bond, a thioether bond, a carbonyl bond, a thiocarbonyl bond, an ester bond, an amide bond, a urethane bond, an imino bond (—N═C(—R)—, —C(═NR)—, wherein R represents a hydrogen atom or an organic group), a carbonate bond, a sulfonyl bond, a sulfinyl bond, an azo bond, and the like.

The bond that includes a hetero atom, which may be included in the organic group represented by each of $R^{b1}$ to $R^{b3}$, is preferably an ether bond, a thioether bond, a carbonyl bond, a thiocarbonyl bond, an ester bond, an amide bond, a urethane bond, an imino bond (—N═C(—R)—, —C(═NR)—, wherein R represents a hydrogen atom or a monovalent organic group), a carbonate bond, a sulfonyl bond, or a sulfinyl bond in view of the heat-resistance of the imidazole compound.

When the organic group represented by each of $R^{b1}$ to $R^{b3}$ is a substituent other than a hydrocarbon group, $R^{b1}$ to $R^{b3}$ are not particularly limited so long as the effects of the invention are not impaired. Specific examples of the atom or group represented by $R^{b1}$ to $R^{b3}$ include a halogen atom, a hydroxyl group, a mercapto group, a sulfide group, a cyano group, an isocyano group, a cyanato group, an isocyanato group, a thiocyanato group, an isothiocyanato group, a silyl group, a silanol group, an alkoxy group, an alkoxycarbonyl group, a carbamoyl group, a thiocarbamoyl group, a nitro group, a nitroso group, a carboxylato group, an acyl group, an acyloxy group, a sulfino group, a sulfonato group, a phosphino group, a phosphinyl group, a phosphonato group, an alkylether group, an alkenylether group, an alkylthioether group, an alkenylthioether group, an arylether group, an arylthioether group, and the like. The hydrogen atom(s) included in the substituent may be substituted with a hydrocarbon group. In addition, the hydrocarbon group included in the substituent may be linear, branched or cyclic.

As $R^{b1}$ to $R^{b3}$, a hydrogen atom, an alkyl group having 1 or more and 12 or less carbon atoms, an aryl group having 6 or more and 12 or less carbon atoms, an alkoxy group having 1 or more and 12 or less carbon atoms, and a halogen atom are preferably, and a hydrogen atom is more preferable.

In the formula (b1), $R^{b4}$ and $R^{b5}$ each independently represent a hydrogen atom, a halogen atom, a hydroxyl group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, or an aliphatic group.

The aliphatic group in $R^{b4}$ and $R^{b5}$ is exemplified by an alkyl group, an alkenyl group, a cycloalkyl group, a cycloalkenyl group, and the like. The aliphatic group may include a hetero atom such as an oxygen atom, a nitrogen atom, or a silicon atom therein. In addition, the aliphatic group may be linear, branched or cyclic.

It is preferable that $R^{b4}$ and $R^{b5}$ each independently represent a hydrogen atom, an alkyl group having 1 or more and 10 or less carbon atoms, a cycloalkyl group having 4 or more and 13 or less carbon atoms, or a cycloalkenyl group having 4 or more and 13 or less carbon atoms, among the atoms and groups described above. More preferably, both of $R^{b4}$ and $R^{b5}$ represent a hydrogen atom, or $R^{b4}$ represents a methyl group and $R^{b5}$ represents a hydrogen atom.

In the formula (b1), $R^{b6}$ represents a hydrogen atom, an alkyl group, or an alkoxy group. $R^{b6}$ has no aromatic group. $R^{b6}$ preferably represents a hydrogen atom, an alkyl group having 1 or more and 10 or less carbon atoms, an alkoxy group having 1 or more and 10 or less carbon atoms. More preferably, $R^{b6}$ represents a hydrogen atom, a methyl group, an ethyl group, a propyl group, a butyl group, a methoxy group, an ethoxy group, a propoxy group, or a butoxy group.

Among the compounds represented by the formula (b1), a compound represented by the following formula (b1-1) is preferable,

[Chem. 7]

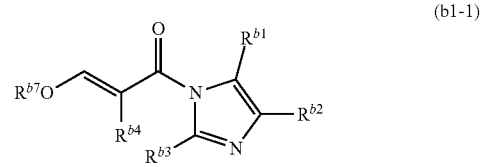

(b1-1)

wherein, in the formula (b1-1), $R^{b1}$ to $R^{b3}$ each independently represent a hydrogen atom, a halogen atom, a hydroxyl group, a mercapto group, a sulfide group, a silyl group, a silanol group, a nitro group, a nitroso group, a sulfonato group, a phosphino group, a phosphinyl group, a phosphonato group, or an organic group; $R^{b4}$ represents a hydrogen atom, a halogen atom, a hydroxyl group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, or an aliphatic group; and $R^{b7}$ represents an alkyl group having 2 or more and 4 or less carbon atoms.

The compound represented by the formula (b1-1) has excellent solubility in an organic solvent because of the presence of the substituent —O—$R^{b7}$. It should be noted that the compound represented by the formula (b1-1) is a novel compound.

$R^{b1}$ to $R^{b4}$ in the formula (b1-1) are the same as $R^{b1}$ to $R^{b4}$ in the formula (b1).

Specific examples of the compound represented by the formula (b1) are shown below.

[Chem. 8]

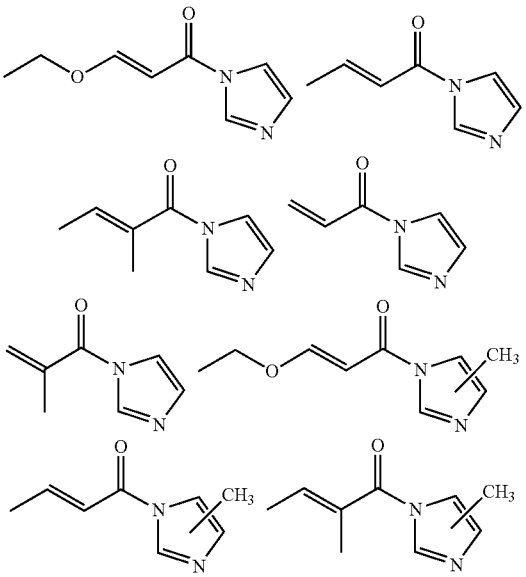

-continued

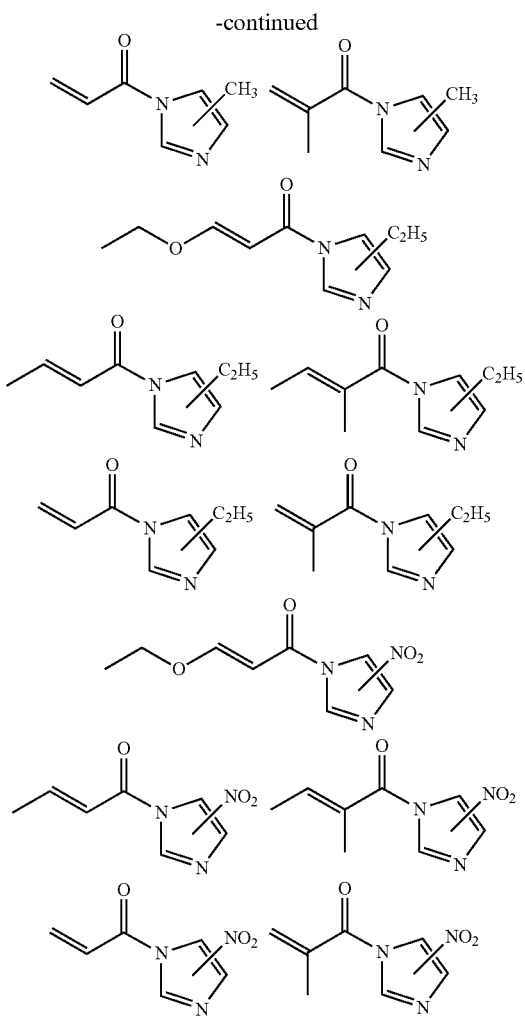

The compound represented by the formula (b1) may be produced by reacting a chloride represented by the following formula (ii) with an imidazole compound represented by the following formula (iii).

[Chem. 9]

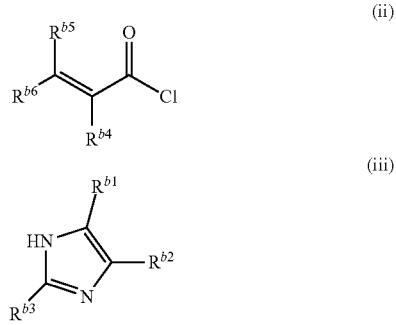

The energy-sensitive composition may contain only one type of the compound represented by the formula (b1), or a combination of two or more types thereof.

The content of the compound represented by the formula (b1) in the energy-sensitive composition is preferably 0.001% by mass or more and 10% by mass or less, more preferably 0.005% by mass or more and 5% by mass or less, and still more preferably 0.01% by mass or more and 1.0% by mass or less. Further, in the energy-sensitive composition, the mass of the compound represented by the formula (b1) is preferably 0.01 parts by mass or more and 10 parts by mass or less, and more preferably 0.1 parts by mass or more and 5 parts by mass or less, when the mass of the polysilane (A) is 100 parts by mass.

[Photo Base Generator]

The energy-sensitive composition contains a photo base generator. The photo base generator can decompose (for example, decarboxylate) with the assistance of light to generates a base. The photo base generator may be an ionic compound or a nonionic compound.

The ionic compound is composed of an anion moiety and a cation moiety. The anion moiety in the ionic compound preferably includes at least one anion selected from the group consisting of an anion having an oxaxanthone skeleton, an anion having a ketoprofen skeleton, and an anion having a fluorenone skeleton. In addition, the cation moiety in the ionic compound preferably includes at least one cation selected from the group consisting of a phosphazene compound cation and an amidine compound cation.

The photo base generator that is an ionic compound is exemplified by a photo base generator represented by the following formula (b2):

[Chem.10]

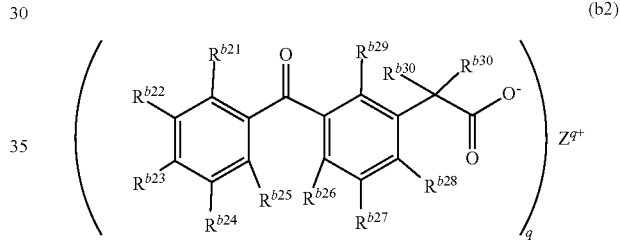

(b2)

wherein, in the formula (b2), $R^{b21}$ to $R^{b31}$ each independently represent a hydrogen atom, a halogen atom, a nitro group, an alkyl group, an aryl group, an arylalkyl group or an alkoxy group, wherein $R^{b25}$ and $R^{b26}$ may be connected to each other via a single bond or a divalent linking group; $Z^{q+}$ represents a q-valent counter cation composed of a base having a pKa of 24 or more; and q represents an integer of 1 or more.

In the compound represented by the above formula (b2), an enol tautomer having an anion moiety shown in the following scheme can exist. The compound represented by the formula (b2) also includes a compound in which the anion moiety is the following enol tautomer.

[Chem. 11]

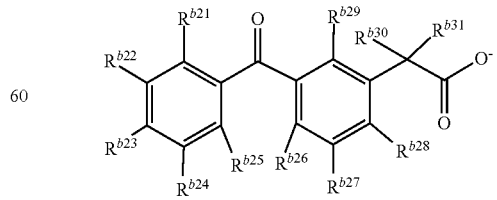

-continued

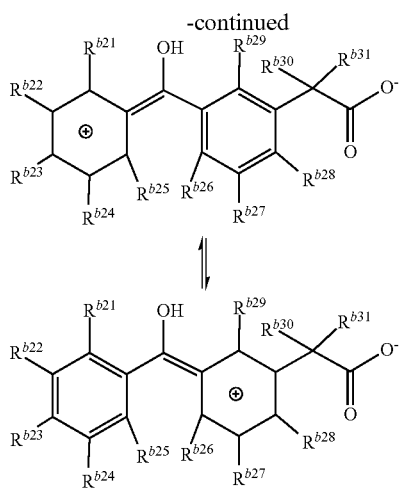

Examples of the halogen atom of $R^{b21}$ to $R^{b31}$ in the formula (b2) include a fluorine atom, a chlorine atom, a bromine atom or an iodine atom, and the halogen atom is preferably a chlorine atom or a bromine atom. Examples of the alkyl group of $R^{b21}$ to $R^{b31}$ include alkyl groups having 1 or more and 12 or less carbon atoms (preferably having 1 or more and 10 or less carbon atoms, and more preferably having 1 or more and 6 or less carbon atoms) which may have a substituent or not, and may be linear, branched or cyclic, and specific examples thereof include a methyl group, an ethyl group, an n-propyl group, an isopropyl group, an n-butyl group, an isobutyl group, a sec-butyl group, a tert-butyl group, a cyclobutyl group, an n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, an n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, an n-heptyl group, an isoheptyl group, a sec-heptyl group, a tert-heptyl group, a neoheptyl group, a cycloheptyl group, an n-octyl group, an isooctyl group, a sec-octyl group, a tert-octyl group, a neooctyl group, a 2-ethylhexyl group, a cyclooctyl group, an n-nonyl group, an isononyl group, a sec-nonyl group, a tert-nonyl group, a neononyl group, a cyclononyl group, an n-decyl group, an isodecyl group, a sec-decyl group, a tert-decyl group, a neodecyl group, a cyclodecyl group, an n-undecyl group, a cycloundecyl group, an n-dodecyl group, a cyclododecyl group, a nonylbonyl group (norbornan-χ-yl group), a bornyl group (bornan-χ-yl group), a menthyl group (menth-χ-yl group), an adamantyl group, a decahydronaphthyl group and the like.

Among the above-mentioned alkyl groups, for example, linear, branched or cyclic alkyl groups having 1 or more and 4 or less carbon atoms, such as a methyl group, an ethyl group, an n-propyl group, an isopropyl group, an n-butyl group, an isobutyl group, a sec-butyl group, a tert-butyl group and a cyclobutyl group are preferable, and alkyl groups having 1 carbon atom such as a methyl group are more preferable.

Examples of the aryl group of $R^{b21}$ to $R^{b31}$ include aryl groups having 6 or more and 14 or less carbon atoms which may be monocyclic or fused polycyclic and may have a substituent or not, such as a phenyl group, a naphthyl group, an anthracenyl group (anthryl group) and a phenanthrenyl group (phenanthryl group). Among these aryl groups, for example, aryl groups having 6 or more and 10 or less carbon atoms, such as a phenyl group and a naphthyl group are preferable, and aryl groups having 6 carbon atoms such as a phenyl group are more preferable.

Examples of the arylalkyl group of $R^{b21}$ to $R^{b31}$ include arylalkyl groups having 7 or more and 15 or less carbon atoms which may have a substituent or not and may be monocyclic or fused polycyclic, such as a benzyl group, a phenethyl group, a methylbenzyl group, a phenylpropyl group, a 1-methylphenylethyl group, a phenylbutyl group, a 2-methylphenylpropyl group, a tetrahydronaphthyl group, a naphthylmethyl group, a naphthylethyl group, an indenyl group, a fluorenyl group, an anthracenylmethyl group (anthrylmethyl group) and a phenanthrenylmethyl group (phenanthrylmethyl group). Among these arylalkyl groups, arylalkyl groups having 7 carbon atoms such as a benzyl group are preferable.

Examples of the alkoxy group of $R^{b21}$ to $R^{b31}$ include alkoxy groups having 1 or more and 12 or less carbon atoms (preferably having 1 or more and 6 or less carbon atoms, and more preferably having 1 or more and 4 or less carbon atoms) which may have a substituent or not and may be linear, branched or cyclic such as a methoxy group, an ethoxy group, an n-propoxy group, an isopropoxy group, an n-butoxy group, an isobutoxy group, a sec-butoxy group, a tert-butoxy group, a cyclobutoxy group, an n-pentyloxy group, an isopentyloxy group, a sec-pentyloxy group, a tert-pentyloxy group, a neopentyloxy group, a 2-methylbutoxy group, a 1,2-dimethylpropoxy group, a 1-ethylpropoxy group, a cyclopentyloxy group, an n-hexyloxy group, an isohexyloxy group, a sec-hexyloxy group, a tert-hexyloxy group, a neohexyloxy group, a 2-methylpentyloxy group, a 1,2-dimethylbutoxy group, a 2,3-dimethylbutoxy group, a 1-ethylbutoxy group, a cyclohexyloxy group, an n-heptyloxy group, an isoheptyloxy group, a sec-heptyloxy group, a tert-heptyloxy group, a neoheptyloxy group, a cycloheptyloxy group, an n-octyloxy group, an isooctyloxy group, a sec-octyloxy group, a tert-octyloxy group, a neooctyloxy group, a 2-ethylhexyloxy group, a cyclooctyloxy group, an n-nonyloxy group, an isononyloxy group, a sec-nonyloxy group, a tert-nonyloxy group, a neononyloxy group, a cyclononyloxy group, an n-decyloxy group, an isodecyloxy group, a sec-decyloxy group, a tert-decyloxy group, a neodecyloxy group, a cyclodecyloxy group, an n-undecyloxy group, a cycloundecyloxy group, an n-dodecyloxy group, a cyclododecyloxy group, a norbornyloxy group (norbornan-χ-yloxy group), a bornyloxy group (bornan-χ-yloxy group), a menthyloxy group (menth-χ-yloxy group), an adamantyloxy group and a decahydronaphthyloxy group. Among these alkoxy groups, for example, linear, branched or cyclic alkoxy groups having 1 or more and 4 or less carbon atoms, such as a methoxy group, an ethoxy group, an n-propoxy group, an isopropoxy group, an n-butoxy group, isobutoxy group, a sec-butoxy group, a tert-butoxy group and a cyclobutoxy group are preferable, and alkoxy groups having 1 carbon atom such as a methoxy group are more preferable.

$R^{b25}$ and $R^{b26}$ may be connected to each other via a single bond or a divalent linking group. Examples of the divalent linking group include an alkylene group, an oxygen atom or a sulfur atom, and the divalent linking group is preferably an oxygen atom. Examples of the alkylene group include linear or branched alkylene groups having 1 or more and 4 or less carbon atoms which may have a substituent or not, and specific examples thereof include a methylene group, an ethylene group, an isopropylene group and the like.

$R^{b21}$ to $R^{b30}$ are more preferably a hydrogen atom and an alkyl group having 1 or more and 12 or less carbon atoms, and still more preferably a hydrogen atom, among others. $R^{b31}$ is more preferably an alkyl group having 1 or more and 12 or less carbon atoms, and still more preferably an alkyl group having 1 or more and 4 or less carbon atoms, among others. $R^{b25}$ and $R^{b26}$ are preferably connected to each other via a divalent linking group. q is preferably an integer of 1 or more and 3 or less, more preferably an integer of 1 or 2, and still more preferably 1.

It should be noted that in the formula (b2), a structure including the oxaxanthone skeleton corresponds to a structure represented by the following formula (b2-1), a structure including the ketoprofen skeleton corresponds to a structure represented by the formula (b2), wherein $R^{b25}$ and $R^{b26}$ are not connected, and a structure including the fluorenone skeleton corresponds to a structure represented by the following formula (b2-2):

[Chem. 12]

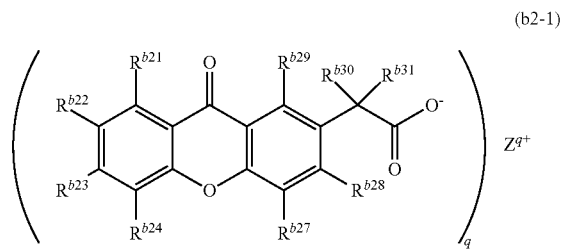

(b2-1)

wherein, in the formula (b2-1), $R^{b21}$ to $R^{b24}$ and $R^{b27}$ to $R^{b31}$, $Z^{q+}$, and q are the same as $R^{b21}$ to $R^{b24}$ and $R^{b27}$ to $R^{b31}$, $Z^{q+}$, and q in the formula (b2), respectively, and

[Chem. 13]

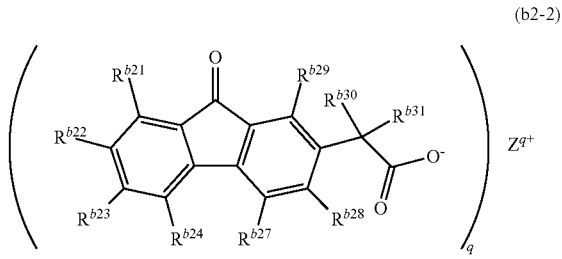

(b2-2)

wherein, in the formula (b2-2), $R^{b21}$ to $R^{b24}$ and $R^{b27}$ to $R^{b31}$, $Z^{q+}$, and q are the same as $R^{b21}$ to $R^{b24}$ and $R^{b27}$ to $R^{b31}$, $Z^{q+}$, and q in the formula (b2), respectively.

In the formula (b2), the q-valent counter cation $Z^{q+}$ is composed of a base having a pKa value of 24 or more (pKa of conjugate acid), preferably 25 or more, more preferably 28 or more, and still more preferably 30 or more. The upper limit of pKa is not particularly limited and is, for example, 50 or less, preferably 45 or less, more preferably 40 or less, and particularly preferably 35 or less.

As used herein, "pKa" means a pKa in an acetonitrile ($CH_3CN$) solvent and is, for example, mentioned in Fourth Revision of Kagaku-Binran II (1993) edited by The Chemical Society of Japan, Maruzen Co., Ltd. The lower this value, the larger the acid strength. Regarding the pKa in $CH_3CN$, it is also possible to determine the value based on a database of Hammett's substituent constant and known literature values by calculation (J. Org. Chem. 2016, 81, 7349-7361).

The base having a pKa of 24 or more constituting the q-valent counter cation $Z^{q+}$ is not particularly limited so long as it has the pKa of 24 or more, and the base includes an organic base or an inorganic base, and is preferably an organic base.

From a viewpoint of basicity and nucleophilicity to a silicon atom, the base having a pKa of 24 or more preferably includes at least one base selected from the group consisting of a phosphazene compound and an amidine compound, namely, the above q-valent counter cation $Z^{q+}$ preferably includes at least one cation selected from the group consisting of a phosphazene compound cation and an amidine compound cation.

(Phosphazene Compound)

As used herein, "phosphazene compound" means "organic compound having a —P═N— bond in the molecule". The number of —P═N— bonds in the above phosphazene compound is not particularly limited so long as the pKa of 24 or more is achieved and includes 1 or more and 10 or less, and is preferably 1 or more and 6 or less, more preferably 1 or more and 5 or less, still more preferably 2 or more and 4 or less, particularly preferably 2 or 3, and most preferably 2. The phosphazene compound is preferably a compound represented by the following formula (bc-1) or a compound in which at least two structures represented by the following formula (bc-1) are connected to each other, and more preferably a compound in which at least two structures represented by the following formula (bc-1) are connected to each other:

[Chem. 14]

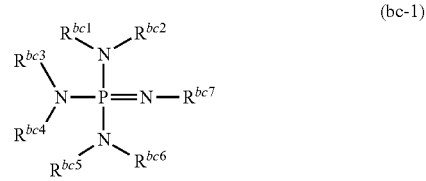

(bc-1)

wherein, in the above formula (bc-1), $R^{bc1}$ to $R^{bc7}$ each independently represent a hydrogen atom or a monovalent organic group which may include a hetero atom, wherein at least two of $R^{bc1}$ to $R^{bc7}$ may be bonded to each other to form a ring. The monovalent organic group which may include a hetero atom of $R^{bc1}$ to $R^{bc7}$ preferably has 1 or more and 20 or less carbon atoms, more preferably 1 or more and 10 or less carbon atoms, and still more preferably 1 or more and 6 or less carbon atoms. Examples of the organic group include an alkyl group, an arylalkyl group and the like, which may include a hetero atom. The alkyl group which may include a hetero atom may be linear, branched or cyclic, and examples thereof include alkyl groups having 1 or more and 12 or less carbon atoms (preferably having 1 or more and 10 or less carbon atoms, and more preferably having 1 or more and 6 or less carbon atoms), and specific examples thereof include a methyl group, an ethyl group, an n-propyl group, an isopropyl group, an n-butyl group, an isobutyl group, a sec-butyl group, a tert-butyl group, a cyclobutyl group, an n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, an n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, an n-heptyl group, an isoheptyl group, a sec-heptyl group, a tert-heptyl group, a neoheptyl group, a cycloheptyl group, an n-octyl group, an isooctyl group, a sec-octyl group, a tert-octyl group, a neooctyl group, a 2-ethylhexyl group, a cyclooctyl group, an n-nonyl group, an isononyl group, a sec-nonyl group, a tert-nonyl group, a neononyl group, a cyclononyl group, an n-decyl group, an isodecyl group, a sec-decyl group, a tert-decyl group, a neodecyl group, a cyclodecyl group, an n-undecyl group, a cycloundecyl group, an n-dodecyl group, a cyclododecyl group, a nonylbonyl group (norbornan-χ-yl group), a bornyl group (bornan-χ-yl group), a menthyl group (menth-χ-yl group), an adamantyl group, a decahydronaphthyl group and the like.

Among the above-mentioned alkyl groups, for example, linear, branched or cyclic alkyl groups having 1 or more and 4 or less carbon atoms such as a methyl group, an ethyl group, an n-propyl group, an isopropyl group, an n-butyl group, an isobutyl group, a sec-butyl group, a tert-butyl group and a cyclobutyl group are preferable.

Examples of the arylalkyl group which may include a hetero atom include arylalkyl groups having 7 or more and 15 or less carbon atoms, and specific examples thereof include a benzyl group, a phenethyl group, a methylbenzyl group, a phenylpropyl group, a 1-methylphenylethyl group, a phenylbutyl group, a 2-methylphenylpropyl group, a tetrahydronaphthyl group, a naphthylmethyl group, a naphthylethyl group, an indenyl group, a fluorenyl group, an anthracenylmethyl group (anthrylmethyl group), a phenanthrenylmethyl group (phenanthrylmethyl group) and the like. Among these arylalkyl groups, arylalkyl groups having 7 carbon atoms, such as a benzyl group are preferable.

Examples of the hetero atom which can be possessed by the monovalent organic group of $R^{bc1}$ to $R^{bc7}$ include a nitrogen atom, an oxygen atom, a phosphorus atom or a sulfur atom. It is preferable that the hetero atom is bonded to a carbon atom and does not constitute an acid functional group such as a carboxyl group or a sulfone group. It is preferable that $R^{bc7}$ is not a hydrogen atom. Examples of the ring which can be formed by at least two of $R^{bc1}$ to $R^{bc7}$ include a five-membered ring, a six-membered ring or a seven-membered ring, and the ring is preferably a six-membered ring.

The compound in which at least two structures represented by the above formula (bc-1) are connected to each other is preferably a compound in which two or more and six or less structures represented by the above formula (bc-1) are connected to each other, more preferably a compound in which two or more and four or less structures represented by the above formula (bc-1) are connected to each other, and still more preferably a compound in which two or three structures represented by the above formula (bc-1) are connected to each other. The aspect in which at least two structures represented by the above formula (bc-1) are connected to each other is preferably an aspect in which one structure represented by the above formula (bc-1) and the other structure represented by the above formula (bc-1) are connected so as to share one nitrogen atom in the above formula (bc-1). A molecular weight (Mw) of the phosphazene compound is, for example, 120 or more and 900 or less, and is preferably 250 or more and 600 or less, and more preferably 300 or more and 500 or less, from the viewpoint of curability or residual film properties.

Preferred specific examples of the phosphazene compound will be exemplified below, but are not limited thereto.

[Chem. 15]

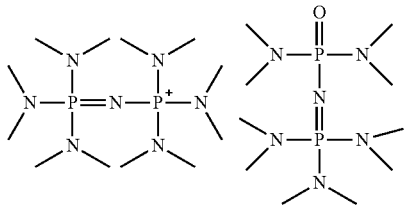

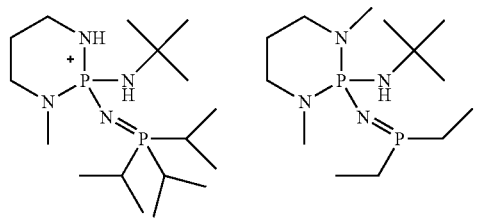

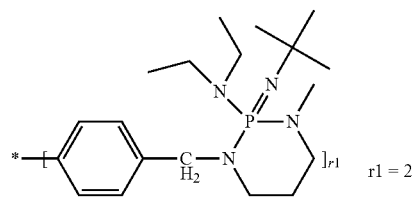

[Chem. 16]

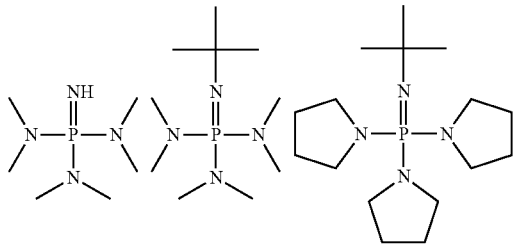

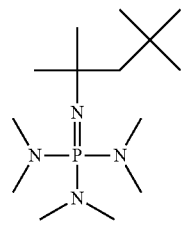

[Chem. 17]

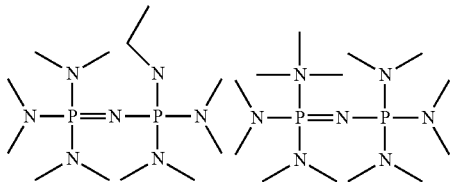

[Chem. 18]

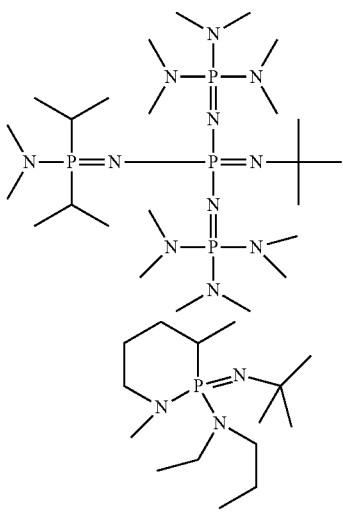

(Amidine Compound)

The amidine compound is preferably a compound represented by the following formula (bc-2):

[Chem. 19]

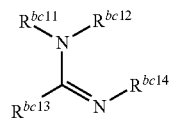

(bc-2)

wherein, in the above formula (bc-2), $R^{bc11}$ to $R^{bc14}$ each independently represent a hydrogen atom or a monovalent organic group which may include a hetero atom, wherein at least one of $R^{bc11}$ to $R^{bc14}$ represents a monovalent organic group which may include a hetero atom, and at least two of $R^{bc11}$ to $R^{bc14}$ may be bonded to each other to form a ring. Specific examples and preferred examples of the monovalent organic group which may include a hetero atom of $R^{bc11}$ to $R^{bc14}$ include those which are the same as mentioned above as the monovalent organic group which may include a hetero atom of $R^{bc1}$ to $R^{bc7}$. Examples of the hetero atom which can be possessed by the monovalent organic group of $R^{bc11}$ to $R^{bc14}$ include a nitrogen atom, an oxygen atom, a phosphorus atom or a sulfur atom. It is preferable that the hetero atom is bonded to a carbon atom and does not constitute an acid functional group such as a carboxyl group or a sulfone group. It is preferable that $R^{bc14}$ is not a hydrogen atom. Examples of the ring which can be formed by at least two of $R^{bc11}$ to $R^{bc14}$ include a five-membered ring, a six-membered ring or a seven-membered ring, and the ring is preferably a six-membered ring or a seven-membered ring. Amidine including at least one ring structure (i.e., cyclic amidine) is preferable. Cyclic amidine including two ring structures (i.e., dicyclic amidine) is more preferable. The amidine compound is more preferably a compound represented by the following formula.

[Chem. 20]

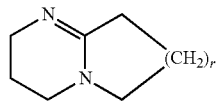

In the above formula, r represents an integer of 1 or more and 3 or less.

Specific examples of the amidine compound include 1,2-dimethyl-1,4,5,6-tetrahydropyrimidine, 1-ethyl-2-methyl-1,4,5,6-tetrahydropyrimidine, 1,2-diethyl-1,4,5,6-tetrahydropyrimidine, 1-n-propyl-2-methyl-1,4,5,6-tetrahydropyrimidine, 1-isopropyl-2-methyl-1,4,5,6-tetrahydropyrimidine, 1-ethyl-2-n-propyl-1,4,5,6-tetrahydropyrimidine, 1-ethyl-2-isopropyl-1,4,5,6-tetrahydropyrimidine, DBU (i.e., 1,8-diazabicyclo[5.4.0]-7-undecene), DBN (i.e., 1,5-diazabicyclo[4.3.0]-5-nonene), TBD (i.e., 1,5,7-triazabicyclo[4.4.0]deca-5-ene) and those analogous thereto, and combinations thereof.

The compound represented by the formula (b2) may be produced by mixing an acid represented by the following formula with the base having a pKa of 24 or more under arbitrary conditions and allowing the reaction (for example, neutralization reaction) to proceed,

[Chem. 21]

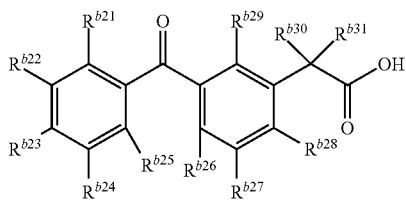

wherein, in the formula, $R^{b21}$ to $R^{b31}$ are the same as $R^{b21}$ to $R^{b31}$ in the formula (b2), respectively.

The photo base generator is composed of the cation moiety and the anion moiety as described above, and with regard to a constitutional molar ratio of the cation moiety and the anion moiety, the cation moiety:anion moiety is, for example, in a range of 1:1 to 1:2, and preferably 1:1 to 1:1.5.

The energy-sensitive composition may contain only one type of the photo base generator or a combination of two or more types thereof.

The proportion of the mass of the compound represented by the formula (b1) is preferably 1% by mass or more and 30% by mass or less, and more preferably 5% by mass or more and 15% by mass or less, based on the sum of the mass of the compound represented by the formula (b1) and the mass of the photo base generator.

The proportion of the mass of the base generator (B) is preferably 0.01% by mass or more and 15% by mass or less, more preferably 0.1% by mass or more and 10% by mass or less, and still more preferably 1% by mass or more and 5% by mass or less, based on the mass of the energy-sensitive composition. The mass of the base generator (B) in the energy-sensitive composition is preferably 0.01 part by mass or more and 30 parts by mass or less, more preferably 0.1 part by mass or more and 20 parts by mass or less, and still more preferably 1 part by mass or more and 15 parts by mass or less, when the mass of the polysilane compound (A) is 100 parts by mass.

It should be noted that the energy-sensitive composition may contain, as the base generator (B), a base generator other than the compound represented by the formula (b1) and the photo base generator (also referred to as other base generator). A thermal base generator other than the compound represented by the formula (b1) falls under the category of the other base generator.

<Acid>

The energy-sensitive composition may further contain an acid so as to improve the stability. From the viewpoint of the homogeneity (compatibility, congeniality), the acid is preferably a conjugate acid of the anion moiety in the base generator represented by the above formula (b2), and specifically an acid represented by the following formula:

[Chem. 22]

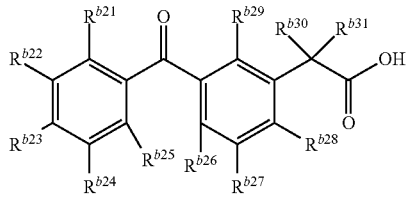

wherein, in the above formula, $R^{b21}$ to $R^{b31}$ are the same as $R^{b21}$ to $R^{b31}$ defined in the above formula (b2), respectively.

Examples of the acid other than the conjugate acid include any organic acid or inorganic acid, and the acid is preferably an organic acid. Examples of the organic acid other than the conjugate acid include monovalent or divalent or higher multivalent organic acid having 1 or more and 30 or less carbon atoms, and specific examples thereof include formic acid, acetic acid, propionic acid, butanoic acid, pentanoic acid, hexanoic acid, heptanoic acid, octanoic acid, nonanoic acid, decanoic acid, oleic acid, stearic acid, linoleic acid, linolenic acid, benzoic acid, phthalic acid, isophthalic acid, terephthalic acid, salicylic acid, trifluoroacetic acid, monochloroacetic acid, dichloroacetic acid, trichloroacetic acid, oxalic acid, malonic acid, methylmalonic acid, ethylmalonic acid, propylmalonic acid, butylmalonic acid, dimethylmalonic acid, diethylmalonic acid, succinic acid, methylsuccinic acid, glutaric acid, adipic acid, itaconic acid, maleic acid, fumaric acid, citraconic acid, citric acid and the like. To maintain the stability, two or more acids may be used in combination.

The energy-sensitive composition may contain the acid described above or not, and when containing the acid, the amount of the acid used is usually 0.001% by mass or more and 10% by mass or less, and preferably 0.01% by mass or more and 5% by mass or less based on the mass of the solid component of the energy-sensitive composition (the mass of the energy-sensitive composition excluding the mass of a solvent).

A use ratio of the entirety of the base generator (B) to the acid in the energy-sensitive composition, for example, in terms of the entirety of the base generator (B):acid is 1:0.003 to 1:3.5, and preferably 1:0.01 to 1:3, in terms of a molar ratio. When the cation moiety is phosphazene, the use ratio of the base generator (B) to the acid in terms of the base generator (B):acid is more preferably 1:0.003 to 1:1 in terms of a molar ratio from the viewpoint of the stability of the energy-sensitive composition. Regarding use of the entirety of the base generator (B) and the acid, an adjustment may be made such that the pH of the energy-sensitive composition is, for example, in a range of 4 or higher and 9 or lower, and preferably 5 or higher and 7 or lower.

<Solvent>

The energy-sensitive composition contains a solvent (S). Examples of the solvent (S) include organic solvents. Specific examples of the organic solvents include: cyclic skeleton-containing acetate compounds represented by the below-mentioned formula (S1), such as cycloalkyl acetate, alcohols such as methanol, ethanol, propanol and n-butanol; polyhydric alcohols such as ethylene glycol, diethylene glycol, propylene glycol and dipropylene glycol; ketones such as acetone, methyl ethyl ketone, cyclohexanone, methyl n-amyl ketone, methyl isoamyl ketone and 2-heptanone; lactone ring-containing organic solvents such as γ-butyrolactone; derivatives of polyhydric alcohols, for example, compounds having an ester bond, such as ethylene glycol monoacetate, diethylene glycol monoacetate, propylene glycol monoacetate or dipropylene glycol monoacetate, and compounds having an ether bond, such as monoalkyl ethers or monophenyl ethers, such as monomethyl ether, monoethyl ether, monopropyl ether and monobutyl ether of the polyhydric alcohols or the compounds having the ester bond; cyclic ethers such as dioxane, and esters such as methyl lactate, ethyl lactate, methyl acetate, ethyl acetate, butyl acetate, methyl pyruvate, ethyl pyruvate, methyl methoxypropionate and ethyl ethoxypropionate; aromatic organic solvents such as anisole, ethyl benzyl ether, cresyl methyl ether, diphenyl ether, dibenzyl ether, phenetole, butyl phenyl ether, ethylbenzene, diethylbenzene, amylbenzene, isopropylbenzene, toluene, xylene, cymene and mesitylene; nitrogen-containing organic solvents such as N,N,N',N'-tetramethylurea, N,N,2-trimethylpropionamide, N,N-dimethylacetamide, N,N-dimethylformamide, N,N-diethylacetamide, N,N-diethylformamide, 1,3-dimethyl-2-imidazolidinone, N-methylpyrrolidone and N-ethylpyrrolidone; and the like.

Among these solvents, cycloalkyl acetate represented by the below-mentioned formula (S1), propylene glycol monomethyl ether acetate (PGMEA), propylene glycol monomethyl ether (PGME), N,N,N',N'-tetramethylurea (TMU) and butanol are preferable, cyclopropyl acetate, cyclobutyl acetate, cyclopentyl acetate, cyclohexyl acetate, cycloheptyl acetate or cyclooctyl acetate is more preferable, and cyclohexyl acetate is still more preferable. These solvents may be used alone or in combination of two or more thereof.

[Chem. 23]

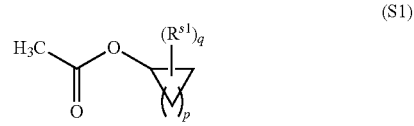

(S1)

In the formula (S1), $R^{s1}$ each independently represent an alkyl group; p is an integer of 1 or more and 6 or less; and q is an integer of 0 or more and (p+1) or less. Examples of the alkyl group represented by $R^{s1}$ include alkyl groups having 1 or more and 3 or less carbon atoms, and specific examples thereof include a methyl group, an ethyl group, an n-propyl group and an i-propyl group.

Specific examples of the cycloalkyl acetate represented by the formula (S1) include cyclopropyl acetate, cyclobutyl acetate, cyclopentyl acetate, cyclohexyl acetate, cycloheptyl acetate and cyclooctyl acetate. Among these, cyclooctyl acetate is preferable from the viewpoint of availability and the like.

The content of the solvent in the energy-sensitive composition is not particularly limited so long as it does not interfere with the object of the present invention. In view of film-forming properties, the solvent is used such that the solid component concentration of the energy-sensitive composition is preferably 0.1% by mass or more and 50% by mass or less, and more preferably 1% by mass or more and 40% by mass or less. The solid component refers to components other than the solvent. The solvent may be used alone or in combination of two or more.

Other Components

The energy-sensitive composition may contain, as a stabilizer, a monohydric or dihydric or higher polyhydric alcohol which has a cyclic ether as a substituent, or an ether compound. Specific examples of a usable stabilizer include stabilizers mentioned in Japanese Unexamined Patent Application, Publication No. 2009-126940, paragraphs (0180) to (0184).

The energy-sensitive composition may contain water. The addition of water leads to an improvement in lithographic performance. The content of water in a solvent component in the energy-sensitive composition is, for example, 0% by mass or more and less than 50% by mass, and preferably 0.5% by mass or more and 5% by mass or less.

The energy-sensitive composition may optionally contain a surfactant. Specific examples of a usable surfactant include surfactants mentioned in Japanese Unexamined Patent Application, Publication No. 2009-126940, paragraph (0185).

<Production Method of Energy-Sensitive Composition>

A production method of the energy-sensitive composition is not particularly limited. For example, the energy-sensitive composition is produced by mixing each component described above with a stirrer or the like. It should be noted that the energy-sensitive composition produced thus may be filtered through a membrane filter, etc. such that the energy-sensitive composition is homogeneous.

Applications

The energy-sensitive composition can be used, for example, in various elements, in applications for formation of a protective film which protects various substrates (including a metal oxide-containing film, a film containing various metals), a sealing material for OLED display element, OLED lightings, hard coats, insulating films, antireflective films, interlayer insulating films, carbon hard masks, display panel materials (flattened films, pixels for color filter, barrier ribs for organic EL, spacers), or a transparent coating film covering a metal wiring in display elements such as touch panels. Examples of various substrates include semiconductor substrates; substrates for display materials (including a metal oxide-containing film, a film containing various metals) such as a liquid crystal display, an organic light-emitting display (OLED), an electrophoretic display (electronic paper), a touch panel, a color filter, and a back light; substrates for solar cells (including a metal oxide-containing film, a film containing various metals); substrates for photoelectric conversion elements (including a metal oxide-containing film, a film containing various metals) such as an optical sensor; and substrates for photoelectric elements (including a metal oxide-containing film, a film containing various metals). In particular, a cured product formed using the energy-sensitive composition has higher hardness. Therefore, the energy-sensitive composition described above is suitably used in applications in which higher hardness is required.

<<Cured Product and Forming Method of Cured Product>>

The energy-sensitive composition described hereinabove may be used to form a cured product. A patterned cured product is typically formed according to a method including the steps of: applying the energy-sensitive composition described above onto a substrate to form a coating film; regioselectively exposing the coating film; developing the exposed coating film; and heating the developed coating film. Hereinafter, each step will be described. The step of applying the energy-sensitive composition onto a substrate to form a coating film is referred to as "coating-film-forming step". The step of regioselectively exposing the coating film is referred to as "exposure step". The step of developing the exposed coating film is referred to as "development step". The step of heating the developed coating film is referred to as "heating step".

<Coating-Film-Forming Step>

A method of applying the energy-sensitive composition to form a coating film is not particularly limited so long as the effects of the present invention are not impaired, and includes a method that involves applying the energy-sensitive composition onto the substrate, using optionally contact transfer coating applicators such as a roll coater, a reverse coater, a bar coater and an inkjet; and non-contact applicators such as a spinner (rotary applicator) and a curtain flow coater. Examples of the substrate include, but are not limited to, a glass substrate, a quartz substrate, a transparent or translucent resin substrate (for example, heat-resistant materials such as polycarbonate, polyethylene terephthalate, polyether sulfone, polyimide, and polyamideimide), metal, a silicon substrate and the like. The substrate may be various substrates, for example, semiconductor substrates, substrates for display materials (including a metal oxide-containing film, a film containing various metals) such as a liquid crystal display, an organic light-emitting display (OLED), an electrophoretic display (electronic paper), a touch panel, a color filter, and a back light; substrates for solar cells (including a metal oxide-containing film, a film containing various metals); substrates for photoelectric conversion elements (including a metal oxide-containing film, a film containing various metals) such as an optical sensor; and substrates for photoelectric devices (including a metal oxide-containing film, a film containing various metals). The thickness of the substrate is not particularly limited and can be appropriately selected according to embodiment of usage of a cured product.

After the application of the energy-sensitive composition, drying (prebaking) is preferably performed. A drying method is not particularly limited and includes, for example, (1) a method that involves drying with a hot plate at a temperature of 80° C. or higher and 180° C. or lower, and preferably 90° C. or higher and 160° C. or lower, for 60 seconds or more and 120 seconds or less, (2) a method that involves allowing to stand at room temperature for several hours to several days, (3) a method that involves placing in a hot-air heater or an infrared heater for several tens of minutes to several hours to remove the solvent, and the like.

<Exposure Step>

In the exposure step, active energy rays such as ultraviolet rays including i-line (365 nm), and excimer laser beams are regioselectively applied to the coating film in accordance with the shape of a desired pattern to conduct the exposure. The exposure causes the base to be generated from the photo base generator. The base generated thus causes an increase in molecular weight of the polysilane (A), etc. to occur, leading to the curing of the exposed portions. Then, a patterned cured product is formed in a subsequent development step.

Light sources emitting ultraviolet rays, such as, e.g., a high pressure mercury lamp, an ultra-high pressure mercury lamp, a xenon lamp and a carbon arc lamp may be employed for the exposure. The regioselective exposure is performed, for example, through a mask having a shape corresponding to the pattern configuration of the cured product. The exposure dose is not particularly limited, and, for example, 30 mJ/cm$^2$ or more and 2,000 mJ/cm$^2$ or less.

<Post-Exposure Baking Step>

Post-exposure baking (PEB), in which the coating film is heated after the exposure and before development, may be performed. PEB is performed, for example, at 80° C. or higher and 180° C. or lower for 30 seconds or more and 120 seconds or less.

<Development Step>

After the exposure step, or after the PEB if the PEB is performed, the development step is performed. In the development step, unexposed portions of the coating film exposed in the exposure step is developed with a developing solution such as an alkaline developing solution or an organic solvent. The developing solution preferably contains an organic solvent. Specific examples of the organic solvent include those which are the same as specific examples of the solvent contained in the energy-sensitive composition.

<Heating Step>

When the developed coating film is heated (baked), a base is generated from the compound represented by the formula (b1). The base generated thus causes an increase in molecular weight of the polysilane (A), etc. to further occur, leading to the formation of a patterned cured product (patterned cured film) having higher hardness.

The heating temperature (baking temperature) may be higher than or equal to a temperature at which the compound represented by the formula (b1) decomposes to generate a base, and is, for example, 250° C. or higher, and preferably 300° C. or higher. The upper limit of the heating temperature is not particularly limited and may be adjusted appropriately according to the substrate or the applications, and is, for example, 1,000° C. or lower, preferably, 700° C. or lower, and more preferably 600° C. or lower. The heating atmosphere is not particularly limited and may be an inert gas atmosphere such as a nitrogen atmosphere or argon atmosphere, or may be under vacuum or reduced pressure. The heating atmosphere may be under an atmospheric air, or the oxygen concentration may be appropriately controlled. The heating time may be appropriately changed, and is 10 minutes or more and 120 minutes or less.

The thickness of the cured product formed thus is preferably 10 nm or more and 10,000 nm or less, and more preferably 50 nm or more and 5,000 nm or less.

Since the energy-sensitive composition described above contains the compound represented by the formula (b1) and the photo base generator along with the polysilane (A), a patterned cured product having higher hardness can be obtained using the energy-sensitive composition. The pencil hardness of the patterned cured product obtained thus is, for example, 3H or higher, preferably 4H or higher.

EXAMPLES

The present invention will be described in more detail by way of Examples, but the present invention is not limited to these Examples.

[Synthesis of Compound Represented by Formula (b1)]

3-Ethoxyacryloyl chloride (4.00 g) as shown in the scheme below was reacted with imidazole (10.40 g) in tetrahydrofuran at room temperature for 240 minutes. Then, the solvent was distilled off from the reaction solution using a rotary evaporator, to yield the following compound b1 (amount=7.78 g, yield=54.00%, yellow solid). The result of $^1$H-NMR measurement of the compound b1 obtained thus is as follows.

$^1$H-NMR (CDCl$_3$): δ (ppm) 8.16 (s, 1H), 7.93 (d, 1H), 7.50 (s, 1H), 7.11 (s, 1H), 5.87 (d, 1H), 4.14 (q, 2H), 1.43 (t, 3H).

[Chem. 24]

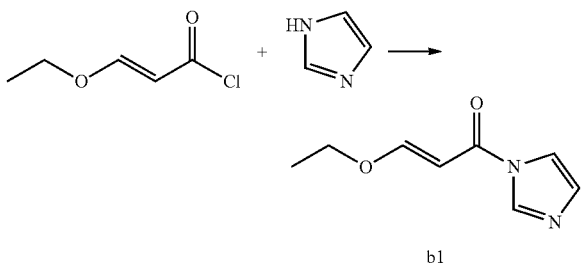

Example 1 and Comparative Examples 1 to 2

In Example and Comparative Examples, a linear polysilane including a silanol group, a phenyl group and a methyl group, in which the silanol group, the phenyl group and the methyl group are each bonded to a silicon atom (mass average molecular weight: 1,500) was used as the polysilane (A).

In Example and Comparative Examples, the compound b1 and the following compound b2, which are a thermal base generator, and the following compound b3, which is a photo base generator, were used. Incidentally, the cation moiety of the compound b3 has a pKa of 33.0.

[Chem. 25]

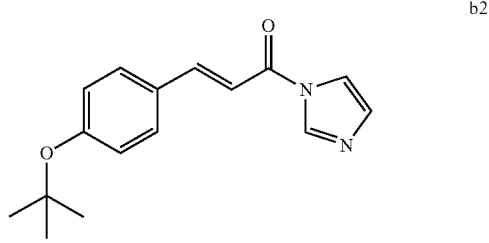

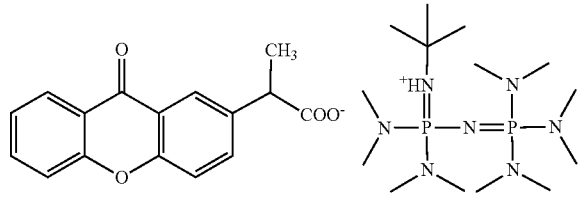

In Example and Comparative Examples, the following s1 was used as a solvent.
s1: Cyclohexyl Acetate (CHXA)

Each of energy-sensitive compositions of Example and Comparative Examples was prepared by dissolving 18.3 parts by mass of the polysilane (A), and the base generator of the type and amount (parts by mass) specified in Table 1 in 80 parts by mass of the solvent, followed by filtration through a filter having a pore size of 0.1 μm made of a fluororesin.

[Preparation of Patterned Cured Product]

Each of the energy-sensitive compositions of the Example and Comparative Examples was applied onto a glass substrate (100 mm×100 mm) using a spin coater, followed by prebaking at 100° C. for 120 seconds, to form a coating film. The coating film obtained thus was subjected to regioselective broadband exposure (wavelength range of 300 nm to 800 nm) at 1,000 mJ/cm² by an ultraviolet aligner using a mask having a line width of 4 μm and a line-and-space of 1:1. The exposed coating film was subjected to heating (PEB) at 140° C. for 120 seconds. The coating film after the PEB was developed for 60 seconds according to a dipping method with cyclohexyl acetate. After the development, the coating film was heated in an atmospheric air at 350° C. for 30 minutes, to yield a line-and-space pattern (patterned cured product) having a thickness of 2 μm.

[Pencil Hardness Evaluation]

Pencil hardness of the patterned cured product obtained in the section [Preparation of Patterned Cured Product] described above was measured using a pencil hardness tester according to ISO 15184, and JIS K 5600-5-4 under the conditions of an angle of 45° and a load of 750 g. The results are shown in Table 1.

[Measurement of Maximum Absorption Wavelength ($\lambda_{max}$)]

The maximum absorption wavelength ($\lambda_{max}$) was determined for the compounds b1 to b3 according to the following method. A solution was prepared by dissolving 1.0 mg of the compound in 1,000 mL of propylene glycol monomethyl ether, and an absorption spectrum (measurement range: 200 nm to 800 nm) of the compound was measured using a spectrophotometer (product name: UV3100PC, from Shimadzu Corporation), and thereby the maximum absorption wavelength was determined. The result was that the maximum absorption wavelength of the compound b1 was 260 nm, the maximum absorption wavelength of the compound b2 was 330 nm, and the maximum absorption wavelength of the photo base generator b3 was 350 nm.

TABLE 1

| | Base generator(B) | | | | |
| | Thermal base generator | | Photo base generator | | |
| | Type | Parts by mass | Type | Parts by mass | Hardness |
|---|---|---|---|---|---|
| Example 1 | b1 | 0.2 | b3 | 1.5 | 4H |
| Comparative Example 1 | b2 | 0.2 | b3 | 1.5 | 2H |
| Comparative Example 2 | — | — | b3 | 1.7 | 6B |

According to the Example, it can be found that the energy-sensitive composition containing the polysilane (A) and the base generator (B), in which the base generator (B) includes the compound represented by the formula (b1) and the photo base generator, yields a cured product having higher hardness. On the other hand, the energy-sensitive composition of Comparative Example 2, which contains the photo base generator but does not contain the compound represented by the formula (b1), and the energy-sensitive composition of Comparative Example 1, which contains a thermal base generator that does not fall under the category of the formula (b1) along with the photo base generator, gave a cured product having lower hardness.

What is claimed is:

1. An energy-sensitive composition comprising a polysilane (A), a base generator (B), and a solvent (S), wherein the base generator (B) comprises a compound represented by formula (b1), and a photo base generator,

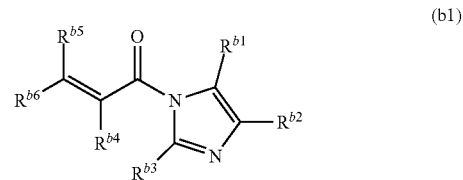

(b1)

wherein $R^{b1}$ to $R^{b3}$ each independently represents a hydrogen atom, a halogen atom, a hydroxyl group, a mercapto group, a sulfide group, a silyl group, a silanol group, a nitro group, a nitroso group, a sulfonato group, a phosphino group, a phosphinyl group, a phosphonato group, or an organic group;

$R^{b4}$ and $R^{b5}$ each independently represents a hydrogen atom, a halogen atom, a hydroxyl group, a mercapto group, a sulfide group, a silyl group, a silanol group, a nitro group, a nitroso group, a sulfino group, a sulfo group, a sulfonate group, a phosphino group, a phosphinyl group, a phosphono group, a phosphonato group, or an aliphatic group; and $R^{b6}$ represents a hydrogen atom, an alkyl group, or an alkoxy group.

2. The energy-sensitive composition according to claim 1, wherein the compound represented by the formula (b1) is represented by formula (b1-1):

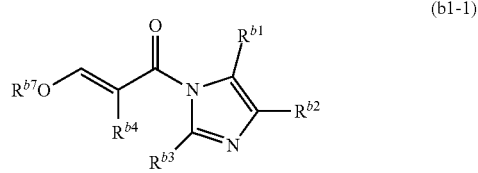

(b1-1)

wherein $R^{b1}$ to $R^{b3}$ each independently represents a hydrogen atom, a halogen atom, a hydroxyl group, a mercapto group, a sulfide group, a silyl group, a silanol group, a nitro group, a nitroso group, a sulfonato group, a phosphino group, a phosphinyl group, a phosphonato group, or an organic group;

$R^{b4}$ represents a hydrogen atom, a halogen atom, a hydroxyl group, a mercapto group, a sulfide group, a silyl group, a silanol group, a nitro group, a nitroso group, a sulfino group, a sulfo group, a sulfonato group, a phosphino group, a phosphinyl group, a phosphono group, a phosphonato group, or an aliphatic group; and $R^{b7}$ represents an alkyl group having 2 or more and 4 or less carbon atoms.

3. The energy-sensitive composition according to claim 1, wherein the photo base generator comprises a photo base generator represented by formula (b2),

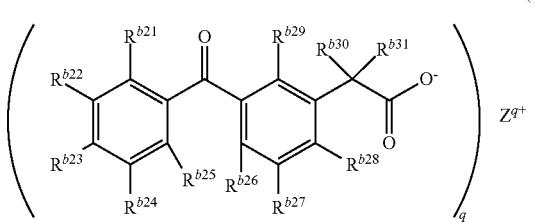

(b2)

wherein $R^{b21}$ to $R^{b31}$ each independently represents represent a hydrogen atom, a halogen atom, a nitro group, an alkyl group, an aryl group, an arylalkyl group, or an alkoxy group, wherein $R^{b25}$ and $R^{b26}$ may be connected to each other via a single bond or a divalent linking group;

$Z^{q+}$ represents a q-valent counter cation composed of a base having a pKa of 24 or more; and q represents an integer of 1 or more.

4. The energy-sensitive composition according to claim 3, wherein the counter cation comprises at least one cation selected from the group consisting of a phosphazene compound cation and an amidine compound cation.

5. The energy-sensitive composition according to claim 4, wherein a phosphazene compound constituting the phosphazene compound cation is a compound represented by formula (bc-1) or a compound in which at least two structures represented by formula (bc-1) are connected to each other, and an amidine compound constituting the amidine compound cation is a compound represented by formula (bc-2):

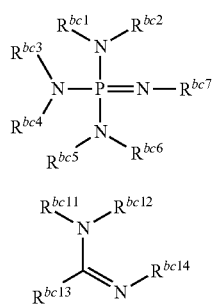

(bc-1)

(bc-2)

wherein in the formula (bc-1), $R^{bc1}$ to $R^{bc7}$ each independently represents a hydrogen atom or a monovalent organic group which may comprise a hetero atom, wherein at least two of $R^{bc1}$ to $R^{bc7}$ may be bonded to each other to form a ring, and wherein in the formula (bc-2), $R^{bc11}$ to $R^{bc14}$ each independently represents a hydrogen atom or a monovalent organic group which may comprise a hetero atom, wherein at least one of $R^{bc11}$ to $R^{bc14}$ represents a monovalent organic group which may comprise a hetero atom, and at least two of $R^{bc11}$ to $R^{bc14}$ may be bonded to each other to form a ring.

6. The energy-sensitive composition according to claim 1, wherein the polysilane (A) comprises a polysilane which comprises at least one of units represented by formulas (a1) and (a2) as an essential unit, and may comprise at least one unit selected from units represented by formulas (a3) to (a5):

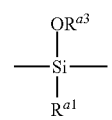

(a1)

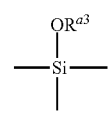

(a2)

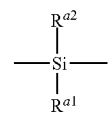

(a3)

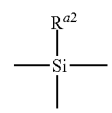

(a4)

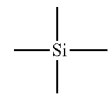

(a5)

wherein in the formulas (a1) to (a5), $R^{a1}$ and $R^{a2}$ represent a hydrogen atom, an organic group or a silyl group; and $R^{a3}$ represents a hydrogen atom or an alkyl group.

7. A cured product of the energy-sensitive composition according to claim 1.

8. A method for forming a patterned cured product, comprising:
applying the energy-sensitive composition according to claim 1 onto a substrate to form a coating film,
regioselectively exposing the coating film,
developing the exposed coating film, and
heating the developed coating film.

* * * * *

UNITED STATES PATENT AND TRADEMARK OFFICE
CERTIFICATE OF CORRECTION

PATENT NO. : 12,099,297 B2  
APPLICATION NO. : 17/452343  
DATED : September 24, 2024  
INVENTOR(S) : Kunihiro Noda, Dai Shiota and Koji Arimitsu Page 1 of 1

It is certified that error appears in the above-identified patent and that said Letters Patent is hereby corrected as shown below:

In the Specification

In Column 16, Lines 60-65, delete: " 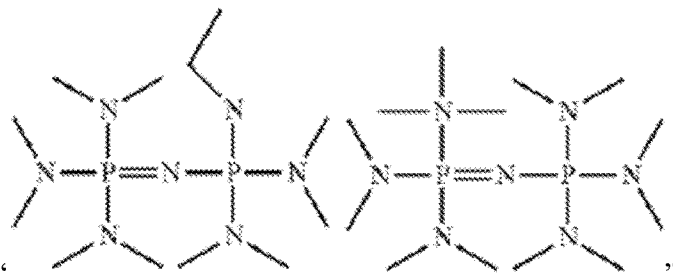 " and insert -- 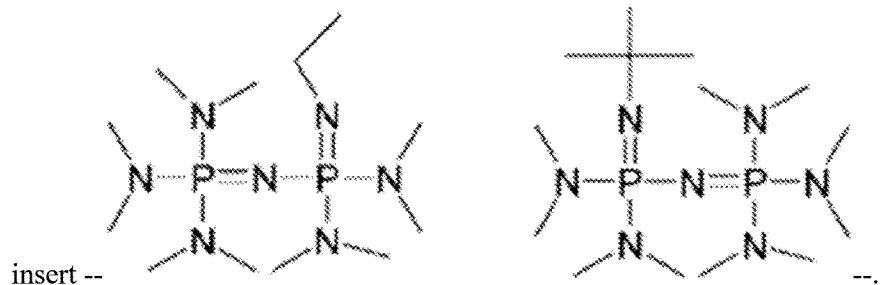 --.

In the Claims

In Column 27, Claim 3, Lines 13-14, delete: "independently represents represent a hydrogen" and insert --independently represents a hydrogen--.

In Column 28, Claim 6, Lines 30-34, delete: " 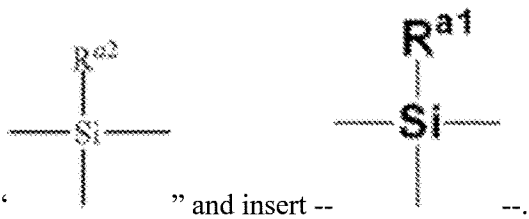 " and insert -- 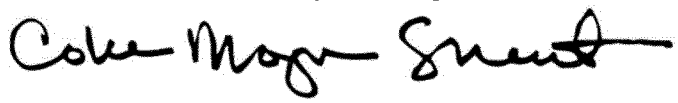 --.

Signed and Sealed this  
Nineteenth Day of August, 2025

Coke Morgan Stewart  
*Acting Director of the United States Patent and Trademark Office*